（12) United States Patent
Barnes et al.

(10) Patent No.: US 9,102,635 B2
(45) Date of Patent: Aug. 11, 2015

(54) SUBSTITUTED BISPHENYL BUTANOIC ACID DERIVATIVES AS NEP INHIBITORS WITH IMPROVED IN VIVO EFFICACY

(71) Applicants: David Weninger Barnes, Waban, MA (US); Dean Franklin Rigel, Berkeley Heights, NJ (US)

(72) Inventors: David Weninger Barnes, Waban, MA (US); Dean Franklin Rigel, Berkeley Heights, NJ (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/178,312

(22) Filed: Feb. 12, 2014

(65) Prior Publication Data

US 2014/0228415 A1    Aug. 14, 2014

Related U.S. Application Data

(60) Provisional application No. 61/764,687, filed on Feb. 14, 2013.

(51) Int. Cl.
C07D 271/113 (2006.01)
A61K 31/4245 (2006.01)
A61K 45/06 (2006.01)

(52) U.S. Cl.
CPC ........ C07D 271/113 (2013.01); A61K 31/4245 (2013.01); A61K 45/06 (2013.01)

(58) Field of Classification Search
USPC ....................................................... 548/144
See application file for complete search history.

(56) References Cited

U.S. PATENT DOCUMENTS

| 4,281,180 | A | 7/1981 | Umezawa et al. |
| 4,610,816 | A | 9/1986 | Berger |
| 4,719,231 | A | 1/1988 | Umezawa et al. |
| 4,721,726 | A | 1/1988 | Berger |
| 4,738,803 | A | 4/1988 | Roques et al. |
| 4,918,105 | A | 4/1990 | Cartwright et al. |
| 5,200,426 | A | 4/1993 | Hersh et al. |
| 5,217,996 | A | 6/1993 | Ksander et al. |
| 5,250,522 | A | 10/1993 | De Lombaert et al. |
| 5,273,990 | A | 12/1993 | De Lombaert et al. |
| 5,294,632 | A | 3/1994 | Erion et al. |
| 5,354,892 | A | 10/1994 | Ksander |
| 5,414,017 | A | 5/1995 | Delaney et al. |
| 5,449,662 | A | 9/1995 | Scarborough |
| 5,517,996 | A | 5/1996 | Okada et al. |
| 5,550,119 | A | 8/1996 | De Lombaert et al. |
| 5,710,171 | A | 1/1998 | Dinsmore et al. |
| 5,891,912 | A | 4/1999 | Kawashima et al. |
| 5,968,980 | A | 10/1999 | Kawashima et al. |
| 6,169,103 | B1 | 1/2001 | Purchase, Jr. et al. |
| 8,263,629 | B2 | 9/2012 | Coppola et al. |
| 8,394,853 | B2 | 3/2013 | Coppola et al. |
| 8,822,534 | B2 | 9/2014 | Iwaki et al. |
| 2002/0193562 | A1 | 12/2002 | Robl |
| 2004/0063761 | A1 | 4/2004 | Kuduk et al. |
| 2008/0119557 | A1 | 5/2008 | Webb et al. |
| 2008/0188533 | A1 | 8/2008 | Choi et al. |
| 2008/0269305 | A1 | 10/2008 | Allegretti et al. |
| 2010/0305131 | A1 | 12/2010 | Coppola et al. |
| 2010/0305145 | A1 | 12/2010 | Coppola et al. |
| 2011/0124695 | A1 | 5/2011 | Iwaki et al. |
| 2012/0122764 | A1 | 5/2012 | Karki et al. |
| 2012/0213806 | A1 | 8/2012 | Fleury et al. |
| 2012/0213807 | A1 | 8/2012 | Fleury et al. |
| 2012/0252830 | A1 | 10/2012 | Coppola et al. |
| 2014/0296240 | A1 | 10/2014 | Coppola et al. |

FOREIGN PATENT DOCUMENTS

| CA | 2 078 590 A1 | 3/1993 |
| EP | 0 038 046 A2 | 10/1981 |
| EP | 0 077 274 A1 | 4/1983 |
| EP | 0 082 088 A1 | 6/1983 |
| EP | 0 103 077 A2 | 3/1984 |
| EP | 0 117 429 A1 | 9/1984 |
| EP | 0 136 883 A2 | 4/1985 |
| EP | 0 214 639 A2 | 3/1987 |
| EP | 0 262 053 A2 | 9/1987 |
| EP | 0 274 453 A2 | 7/1988 |

(Continued)

OTHER PUBLICATIONS

[No Author Listed] Library compound: RN:144139-09-3. Substance Identifier task started on Monday Jun 20, 2011 at 12:51 Pm. Explored by Substance Identifier in Registry.

(Continued)

*Primary Examiner* — Nyeemah A Grazier
(74) *Attorney, Agent, or Firm* — Sophie Binet Cross

(57) ABSTRACT

The present invention provides a compound of formula I;

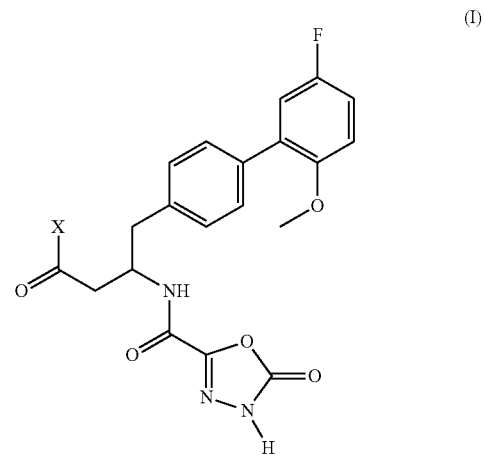

or a pharmaceutically acceptable salt thereof, wherein X is defined herein. The invention also relates to a method for manufacturing the compounds of the invention, and its therapeutic uses. The present invention further provides pharmaceutical composition of the compounds of the invention and a combination of pharmacologically active agents and a compound of the invention.

15 Claims, 2 Drawing Sheets

(56) References Cited

FOREIGN PATENT DOCUMENTS

| EP | 0 356 124 A2 | 2/1990 |
|---|---|---|
| EP | 0 497 192 A2 | 8/1992 |
| EP | 0 533 130 A1 | 9/1992 |
| EP | 0 534 492 A2 | 3/1993 |
| EP | 1 903 027 A1 | 3/2008 |
| EP | 2 070 928 A1 | 6/2009 |
| FR | 2 597 865 A1 | 4/1986 |
| GB | 2 037 754 | 7/1980 |
| GB | 2 207 351 | 2/1999 |
| GB | 2 354 440 A2 | 3/2001 |
| JP | 41-49166 A | 5/1992 |
| JP | 52-62709 A | 10/1993 |
| JP | 62-34630 A | 8/1994 |
| JP | 71-57459 A | 6/1995 |
| JP | 2000-344614 A | 12/2000 |
| JP | 2003-321358 A | 11/2003 |
| WO | 91/02718 A1 | 3/1991 |
| WO | 91/09840 A1 | 7/1991 |
| WO | 94/20457 A1 | 9/1994 |
| WO | 95/35307 A1 | 12/1995 |
| WO | 97/43249 A1 | 11/1997 |
| WO | 97/47270 A3 | 12/1997 |
| WO | 98/09940 A1 | 3/1998 |
| WO | 98/18803 A1 | 5/1998 |
| WO | 98/53817 A1 | 12/1998 |
| WO | 99/26921 A1 | 6/1999 |
| WO | 99/26922 A1 | 6/1999 |
| WO | 99/26923 A1 | 6/1999 |
| WO | 99/36393 A1 | 7/1999 |
| WO | 02/26696 A1 | 4/2002 |
| WO | 03/059345 A1 | 7/2003 |
| WO | 2004/062553 A2 | 7/2004 |
| WO | 2004/099171 A2 | 11/2004 |
| WO | 2005/012270 A2 | 2/2005 |
| WO | 2005/014534 A1 | 2/2005 |
| WO | 2006/020358 A2 | 2/2006 |
| WO | 2006/055725 A2 | 5/2006 |
| WO | 2006/069096 A1 | 6/2006 |
| WO | 2006/086456 A2 | 8/2006 |
| WO | 2007/045663 A2 | 4/2007 |
| WO | 2007/056324 A2 | 5/2007 |
| WO | 2007/056546 A1 | 5/2007 |
| WO | 2008/031567 A1 | 3/2008 |
| WO | 2008/073138 A2 | 6/2008 |
| WO | 2008/083967 A2 | 7/2008 |
| WO | 2008/138561 A1 | 11/2008 |
| WO | 2008/153857 A1 | 12/2008 |
| WO | 2009/061713 A1 | 5/2009 |
| WO | 2009/076288 A1 | 6/2009 |
| WO | 2009/090251 A2 | 7/2009 |
| WO | 2010/011821 A2 | 1/2010 |
| WO | 2010/136493 A1 | 12/2010 |
| WO | 2011/035569 A1 | 3/2011 |
| WO | WO2011137734 A1 * | 11/2011 ........... A61K 31/485 |
| WO | 2012/082853 A1 | 6/2012 |

OTHER PUBLICATIONS

Bhagwat et al.; "Alpha-Mercaptoacyl Dipeptides That Inhibit Angiotensin Converting Enzyme and Neutral Endopeptidase 24.11."; Bioorganic & Medicinal Chemistry Letters; 5(7):735-738 (1995).
Bouboutou et al.; "Bidentate Peptides : Highly Potent New Inhibitors of Enkephalin Degrading Enzymes"; Life Sciences; 35(9):1023-1030 (1984).
Bourdel; New Hydroxamate Inhibitors of Neurotensin-Degrading Enzymes: synthesis and Enzyme Active-site recognition; International Journal of Peptide & Protein Research; 1996, 48(2) 148-155.
Davies; "First asymmetric synthesis of the Kelatorphan-like enkephalinase inhibitor (1S,2R,29S)-2-[29-(N-hydroxycarbamoylmethyl)-39-phenylpropionylamino]cyclohexane-1-carboxylic acid"; Journal of the Chemical Society, Perkin Transactions 1: Organic and Bio-Organic Chemistry (1998), vol. 17; pp. 2629-2634.

De Lombaert et al., "Dual Inhibition of Neutral Endopeptidase and Angiotensin-Converting Enzyme by N-Phosphonomethyl and N-Carboxyalkyl Dipeptides," Bioorganic & Medicinal Chemistry Letters 4(22):2715-2720 (1994).
De Lombaert et al., "Non-Peptidic Inhibitors of Neutral Endopeptidase," Bioorganic and Medicinal Chemistry Letters 5 (2):145-150 (1995).
De Lombaert et al.; "Chemical and Plasma Hydrolyses of a Diphenyl Alpha-Aminomethyl Phosphonate Prodrug Inhibitor of Neutral Endopeptidase 24.11"; Bioorganic & Med. Chem. Ltrs.; 4(7):899-902 (1994).
De Lombaert et al.; "Non-Peptidic Inhibitors of Neutral Endopeptidase 24.11-2. Design and Pharmacology of Orally Active Phosphonate Prodrugs"; Bioorganic & Medicinal Chemistry Letters; 5(2):151-154 (1995).
De Lombaert et al.; "N-Phosphonomethyl Dipeptides and Their Phosphonate Prodrugs, a New Generation of Neutral Endopeptidase (NEP, EC 3.4.24.11) Inhibitors1"; J. Med. Chem.; 37(4):498-511 (1994).
Deaton et al.; "Thiol-based angiotensin-converting enzyme 2 inhibitors: P1' modifications for the exploration of the S1 subsite"; Bioorganic & Medicinal Chemistry Letters; 18:1681-1687 (2008).
Deaton et al.; "Thiol-based angiotensin-converting enzyme 2 inhibitors: P1 modifications for the exploration of the S1 subsite"; Bioorganic & Medicinal Chemistry Letters; 18:732-737 (2008).
Doulut, et al.: "Synthesis and analgesic effects of N-[3-[(hydroxyamino)carbonyl]-1-oxo2(R)-benzylpropyl]-L-isoleucyl-L-leucine, a new potent inhibitor of multiple neurotensin/neuromedin N degrading enzymes" J. Med. Chem. 1993,36, pp. 1369-1379.
Fournie-Zaluski et al., "Differential Recognition of "Enkephalinase" and ANgiotensin-Converting Enzyme by New Carboxyalkyl Inhibitors," Life Sciences 31:2947-2954 (1982).
Fournie-Zaluski et al., "Synthesis and biological properties of highly potent enkephalinase inhibitors," Dep. Chim. Org., CNRS, Paris 75006 FR. Pept. Proc. Eur. Pept. Symp., 16th, Meeting date 1980, 476-481 (1981).
Fournie-Zaluski, et al; "Development of [125I]RB104, a potent inhibitor of neutral endopeptidase 24.11, and its use in detecting nanogram quantities of the enzyme by inhibitor gel electrophoresis" Proc. Nadl. Acad. Sci. USA vol. 89, pp. 6388-6392, (1992).
Fournie-Zaluski; "Analgesic Effects of Kelatorphan, A New Highly Potent Inhibitor of Multiple Enkephalin Degrading Enzymes"; European Journal of Pharmacology, 102 (1984) 525-528.
Fournie-Zaluski; "Enkephalin-degrading enzyme inhibitors. Crucial role of the C-terminal residue on the inhibitory potencies of retro-hydroxamate dipeptides": International Journal of Peptide & protein research (1989), 33(2), pp. 146-153.
Fourni-Zaluski: "New Carboxyalkyl Inhibitors of Brain Enkephalinase: Synthesis, Biological Activity, and Analgesic Properties"; J. Med. Chem. 1983,26, 60-65.
"Golub et al., Molecular classification of cancer: class discovery and class prediction by gene expressionmonitoring. Science. Oct. 15, 1999;286(5439):531-7."
"Hachisu et al., Relationship between enhancement of morphine analgesia and inhibition of enkephalinase by 2S, 3R 3-amino-2-hydroxy-4-phenylbutanoic acid derivatives. Life Sci. May 17, 1982;30(20):1739-46."
Hanessian et al.; "Targeting ACE and ECE with dual acting inhibitors"; Bioorganic & Medicinal Chemistry Letters; 18:1058-1062 (2008).
Hernandez: "Retro-Inverso Concept Applied to the Complete Inhibitors of Enkephalin-Degrading Enzymes"; J. Med. Chem. 1988,31, 1825-1831.
Jeng et al.; "CGS 34226, a thiol-based dual inhibitor of endothelin converting enzyme-I and neutral endopeptidase 24.11"; Clinical Science; 103(Suppl. 48):98S-101S [Printed in Great Britain] (2002).
Kanno,"Synthesis and Evaluation of 2-(Biphenylmethyl)Glutaric Acid Amide Derivatives as Neutral Endopeptidase Inhibitors"; Bioorganic medicinal chemistry letters 1996; vol. 6; No. 13; pp. 1487-1490.
Ksander,; "Dicarboxylic Acid Dipeptide Neutral Endopeptidase Inhibitors"; J. Med. Chem. 1995,38, 1689-1700.

(56) References Cited

OTHER PUBLICATIONS

Ksander; "Enkephalinase Inhibitors. 1. 2,4-Dibenzylglutaric Acid Derivatives"; J. Med. Chem. 1989,32, 2519-2526.

Lala et al., Role of nitric oxide in tumor progression: lessons from experimental tumors. Cancer Metastasis Rev. Mar. 1998;17(1):91-106.

Matsuoka; 2S,3R 3-Amino-2-hydroxy-4-phenylbutanoic acid derivatives, enkephalinase inhibitors, augment Met5-enkephalin-induced antinociception: Japanese Journal of Pharmacology (1988); vol. 46(3); pp. 205-210.

Milhiet; "Increase of Neutral endopeptidase—24.11 with cellular density and enzyme modulation with an inhibitor on human Reh6 cell line", Biochemical Pharmacology, vol. 43, No. 8, pp. 1711-1715, (1992).

Patani et al., Bioisosterism: A Rational Approach in Drug Design. Chem Rev. Dec. 19, 1996;96(8):3147-3176.

Patent Publication No. 2012-0122977, published May 17, 2012, U.S. Appl. No. 13/294,262, filed Nov. 11, 2011—Office Action dated Aug. 8, 2013 and response to same, dated Sep. 16, 2013.

Rogues: "New enkephalinase inhibitors as probes to diferentiate enkephalinase and angiotensin-converting enzyme active sites"; Life Sciences, vol. 31, pp. 1749-1752.

Tejedor-Real; "Effect of Mixed (RB 38A) and Selective (RB 38B) Inhibitors of Enkephalin Degrading Enzymes on a Model of Depression in the Rat": Biol Psychiatry;1993;34: pp. 100-107.

Wallace et al., "Design and Synthesis of Potent, Selective Inhibitors of Endothelin-Converting Enzyme," Journal of Medicinal Chemistry 41:1513-1523 (1998).

Xie: "New Kelatorphan-Related Inhibitors of Enkephalin Metabolism: Improved Antinociceptive Properties": J. Med. Chem. 1989,32, 1497-1503.

Xie: "Inhibitors of the enkephalin degrading enzymes. Modulation of activity of hydroxamate containing compounds by modifications of the C-terminal residue"; International Journal of Peptide & Protein Research (1989), 34(3); pp. 246-255.

Xie: "New inhibitors of enkephalin-degrading enzymes"; Colloque INSERM (1989), 174(Foru, Pept., 2nd, 1988), pp. 349-352.

Yao et al., "Potent P1' biphenylmethyl substituted aggrecanase inhibitors" Bioorganic & Medicinal Chemistry Letters 12:101-104 (2002).

Park et al., Therapeutic Potential of Atrial Natriuretic Peptide administration on Peripheral Arterial Diseases, Endocrinology 149(2):483-491 (2008).

Yamahara et al., "Significance and therapeutic potential of the natriuretic peptides/cGMP/cGMP-dependent protein kinase pathway in vascular regeneration", PNAS, 100(6):3404-3409 (2003).

Tokudome et al., "Impaired Recovery of Blood Flow After Hind-limb Ischemia in Mice Lacking Guanylyl Cyclase-A, a receptor for Atrial and Brain Natriuretic Peptides", Arterioscler Thromb Vase Biol 29:1516-1521 (2009).

* cited by examiner

SUBSTITUTED BISPHENYL BUTANOIC ACID DERIVATIVES AS NEP INHIBITORS WITH IMPROVED IN VIVO EFFICACY

This application claims benefit under 35 U.S.C. §119(e) of U.S. Provisional Application No. 61/764,687, filed Feb. 14, 2013; the content of which is incorporated herein by reference in their entirety.

FIELD OF THE INVENTION

The invention provides neutral endopeptidase (EC 3.4.24.11) (NEP) inhibitor compounds, the use thereof for inhibiting NEP and methods of treating disease using same.

BACKGROUND OF THE INVENTION

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase EC 3.4.24.11, also responsible for e.g., the metabolic inactivation of enkephalins.

Neutral endopeptidase (also known as NEP, endopeptidase 24.11, EC 3.4.24.11; neprilysin, enkephalinase; atriopeptidase; fibroblast metalloelastase, kidney-brush-border neutral peptidase, membrane metallopeptidase A, MME g.p. (*homo sapiens*), common acute lymphocytic leukemia antigen (CALLA) or CD antigen (CD10)) is a zinc-containing metalloprotease found in many organs and tissues including brain, kidneys, lungs, gastrointestinal tract, heart and peripheral vasculature. NEP cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide, brain natriuretic peptide (BNP), met- and leu-enkephalin, bradykinin, neurokinin A, endothelin-1, angiotensins, adrenomedullin, glucagon-like peptides, glucagon, insulin B chain, amyloid betas and substance P. Some of these peptides have potent vasodilatory and neurohormone functions, diuretic and natriuretic activity or mediate behaviour effects. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, neutral endopeptidase inhibitors should increase plasma levels of ANP and, hence, are expected to induce natriuretic and diuretic effects.

Furthermore, NEP enzyme plays an important role in blood pressure homeostasis and cardiovascular health.

NEP inhibitors have been reported in U.S. Pat. No. 5,217, 996; WO 2010/136474; WO 2010/136493; WO 2011/061271; WO 2012/065953, WO2012/082853 and WO 2012/065956. Despite the disclosure of various NEP inhibitors, there is a need in the art for NEP inhibitors with improved in vivo activity.

SUMMARY OF THE INVENTION

The aim of the present invention is to provide novel compounds with improved in vivo potency which are useful as neutral endopeptidase inhibitors, e.g., as inhibitors of the ANF-degrading enzyme in mammals, so as to prolong and potentiate the diuretic, natriuretic and vasodilator properties of ANF in mammals, by inhibiting the degradation thereof to less active metabolites.

The compounds of this invention are thus particularly useful for the treatment of conditions and disorders responsive to the inhibition of neutral endopeptidase.

The compounds of the invention have unexpected improved in vivo neutral endopeptidase inhibitory activity compared to compounds of WO 2010/136493.

The invention pertains to the compounds, pharmaceutical compositions and methods of use thereof as described herein. Examples of compounds of the invention include the compounds according to any one of Formulae I to III, or a pharmaceutically acceptable salt thereof and the compounds of the examples.

In embodiment 1, the invention therefore provides a compound of the formula (I):

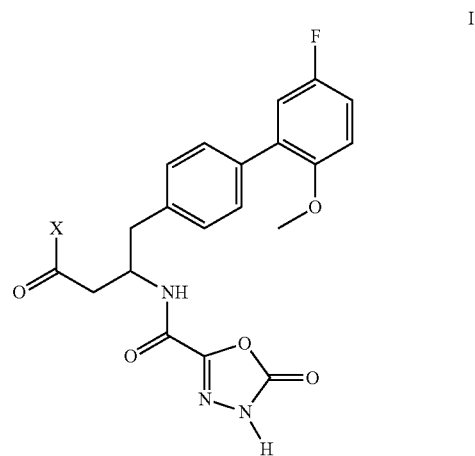

wherein:
X is OH, O—$C_{1-7}$alkyl or O—$C_{6-10}$aryl; or
a pharmaceutically acceptable salt thereof.

The compounds of the invention, by inhibiting the neutral endopeptidase, can potentiate the biological effects of bioactive peptides. Thus, in particular the compounds have utility in the treatment of a number of disorders, including hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria and ascites. In addition, because of their ability to potentiate the effects of ANF the compounds have utility in the treatment of glaucoma. As a further result of their ability to inhibit the neutral endopeptidase the compounds of the invention may have activity in other therapeutic areas including for example the treatment of menstrual disorders, preterm labour, pre-eclampsia, endometriosis, and reproductive disorders (especially male and female infertility, polycystic ovarian syndrome, implantation failure). Also the compounds of the invention should treat asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications, atherosclerosis and male and female sexual dysfunction.

In a preferred embodiment the compounds of the invention are useful in the treatment of cardiovascular disorders.

In another embodiment, the invention pertains to a method for treating a disorders or diseases responsive to the inhibition of neutral endopeptidase, in a subject in need of such treatment, comprising: administering to the subject an effective amount of a compound according to any one of Formulae I-III, or a pharmaceutically acceptable salt thereof, such that the disorder or disease responsive to the inhibition of neutral endopeptidase in the subject is treated.

In yet another embodiment, the invention pertains to pharmaceutical compositions, comprising a compound according to any one of Formulae I-III, or a pharmaceutically acceptable salt thereof, and one or more pharmaceutically acceptable carriers.

In still another embodiment, the invention pertains to combinations including, a compound according to any one of Formulae I to III, or a pharmaceutically acceptable salt thereof, and pharmaceutical combinations of one or more therapeutically active agents.

In another embodiment, the invention pertains to a method for inhibiting neutral endopeptidase in a subject in need thereof, comprising: administering to the subject a therapeutically effective amount of a compound according to any one of Formulae I-III, or a pharmaceutically acceptable salt thereof, such that neutral endopeptidase is inhibited.

DETAILED DESCRIPTION OF THE INVENTION

Definition

Figure 1:
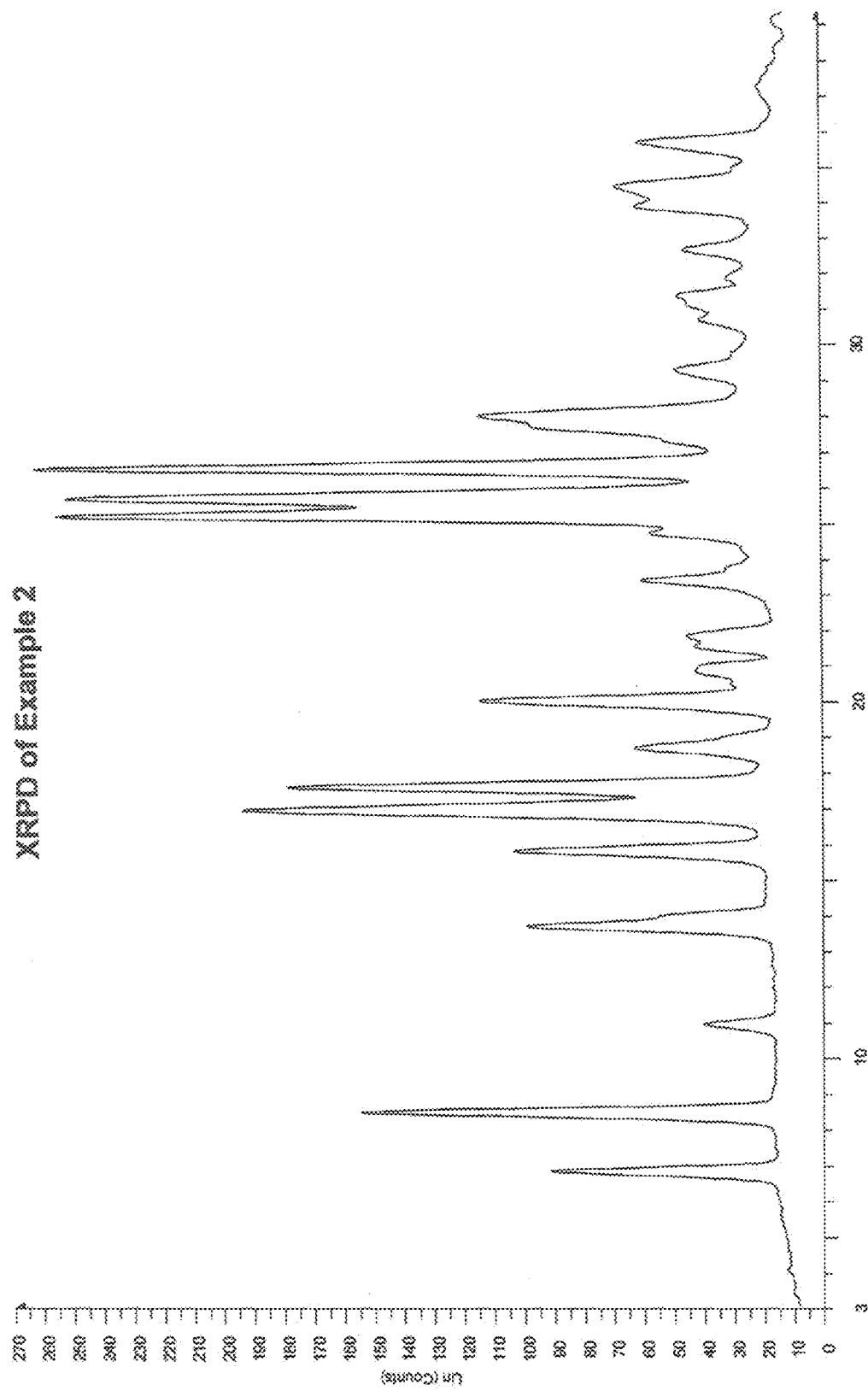
FIG. 1. illustrates the x-ray powder diffraction patterns of Example 2.

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 7 carbon atoms. Preferably the alkyl comprises 1 to 4 carbon atoms. Representative examples of alkyl include methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-7}$alkyl" refers to a hydrocarbon having from one to seven carbon atoms.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "$C_{6-10}$ aryl" refers to an aromatic hydrocarbon group having 6 to 10 carbon atoms in the ring portion. The term aryl refers to substituted and unsubstituted aryl. Examples of substituents are halo, $C_{1-7}$alkyl, halo-$C_{1-7}$alkyl, $C_{1-7}$alkoxy.

As used herein, the term "cycloalkyl" refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons. The term "$C_{1-7}$alkoxy" refers to an alkoxy group having from one to seven carbon atoms.

Compound of the Invention:

Various embodiments of the invention are described herein. It will be recognized that features specified in each embodiment may be combined with other specified features to provide further embodiments.

In embodiment 2, certain compounds of Formula I have the (R) stereochemistry and are represented by compounds of Formula II:

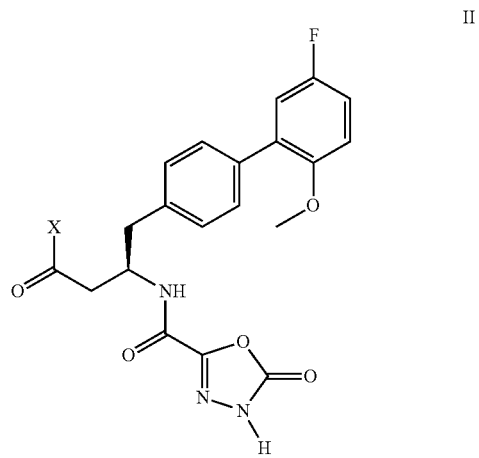

II

X is OH, O—$C_{1-7}$alkyl or O—$C_{6-10}$aryl; or
a pharmaceutically acceptable salt thereof.

In one aspect of embodiment 2, the invention pertains to compounds of Formula II wherein X is O—$C_{1-7}$alkyl or O—$C_{6-10}$aryl, or a pharmaceutically acceptable salt thereof. In a further aspect of this embodiment, X is O—$C_{1-7}$alkyl, preferably ethyl.

In embodiment 3, the invention pertains to compounds of Formula III:

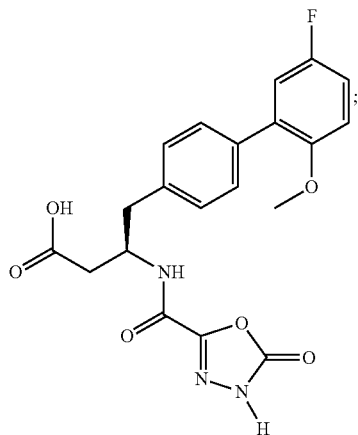

or a pharmaceutically acceptable salt thereof.

In embodiment 4, the invention pertains to compounds of Formula I or II wherein X is —OMe, OEt or O-indanyl; or a pharmaceutically acceptable salt thereof.

In another embodiment individual compounds according to the invention are those listed in the Examples section below or a pharmaceutically acceptable salt thereof.

In embodiment 5, the invention is crystalline form A of Example 2.

In embodiment 6, the invention is crystalline form A of Example 2 characterized by a x-ray powder diffraction pattern comprising four or more 2θ values (CuKα λ=1.5418 Å) selected from the group consisting of 6.8±0.2°, 8.5±0.2°, 13.7±0.2°, 15.8±0.2°, 17.0±0.2°, 17.6±0.2°, 20.0±0.2°, 25.3±0.2°, 25.8±0.2°, 26.6±0.2°, 27.8±0.2° and 28.1±0.2° measured at a temperature of about 22° C. and an x-ray wavelength, λ, of 1.5418 Å.

In embodiment 7, the invention is crystalline form A of Example 2 characterized by a x-ray powder diffraction pattern comprising five or more 2θ values (CuKα λ=1.5418 Å) selected from the group consisting of 6.8±0.2°, 8.5±0.2°, 13.7±0.2°, 15.8±0.2°, 17.0±0.2°, 17.6±0.2°, 20.0±0.2°, 25.3±0.2°, 25.8±0.2°, 26.6±0.2°, 27.8±0.2° and 28.1±0.2° measured at a temperature of about 22° C. and an x-ray wavelength, λ, of 1.5418 Å.

In embodiment 8, the invention is crystalline form A of Example 2 having an X-ray diffraction spectrum substantially the same as the X-ray powder diffraction spectrum shown in FIG. 1.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Occasionally, the variability could be higher than 0.2° due to apparatus calibration differences. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measure only.

Figure 2:
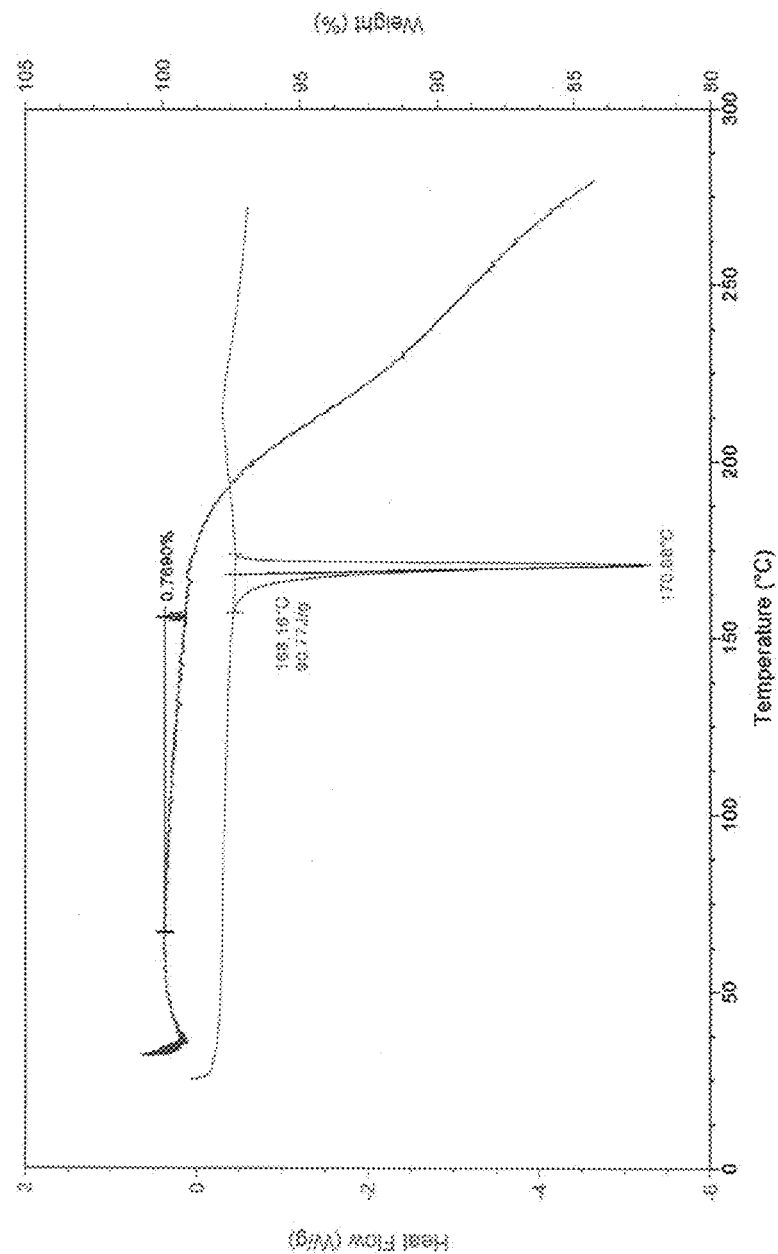
FIG. 2. illustrates the differential scanning calorimetry (DSC) and thermogravimetric analysis (TGA) of Example 2.

In embodiment 9, the invention is crystalline form A of Example 2 having a differential scanning calorimetry (DSC) thermogram substantially the same as that shown in shown in FIG. 2.

In embodiment 10, the invention is crystalline form A of Example 2 having a thermo gravimetric analysis (TGA) diagram substantially the same as that shown in shown in FIG. 2.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" and "diastereomers" are used interchangeably and are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R), (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O' p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atoms may be enriched in $^2$H; or/and one or more carbon atom may be enriched in $^{11}$C, $^{13}$C $^{14}$C; or/and one or more nitrogens may be enriched in $^{14}$N. Such isotopically labeled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae I to III. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically enriched compounds of formulae I to III can generally be prepared by conventional techniques known to those skilled in the art or by processes analogous to those described in the accompanying Examples and Preparations using an appropriate isotopically enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e., compounds according to any one of formulae I to III that contain groups capable of acting as donors and/or acceptors for hydrogen bonds may be capable of forming co-crystals with suitable co-crystal formers. These co-crystals may be prepared from compounds according to any one of formulae I to III by known co-crystal forming procedures. Such procedures include grinding, heating, co-subliming, co-melting, or contacting in solution compounds according to any one of formulae I to III with the co-crystal former under crystallization conditions and isolating co-crystals thereby formed. Suitable co-crystal formers include those described in WO 2004/078163. Hence the invention further provides co-crystals comprising a compound according to any one of formulae I to III or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease or a symptom thereof (i) ameliorated by the inhibition of neutral endopeptidase or (ii) associated with neutral endopeptidase activity, or (iii) characterized by abnormal activity of neutral endopeptidase; or (2) reduce or inhibit the activity of neutral endopeptidase; or (3) reduce or inhibit the expression of neutral endopeptidase. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of neutral endopeptidase; or at least partially reduce or inhibit the expression of neutral endopeptidase.

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that convert in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity.

Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids. Suitable prodrugs are often pharmaceutically acceptable ester derivatives convertible by solvolysis under physiological conditions to the parent carboxylic acid, e.g., lower alkyl esters, aryl esters and the like conventionally used in the art.

Furthermore, the compounds of the present invention, including their salts, can also be obtained in the form of their hydrates, or include other solvents used for their crystallization.

General Synthetic Scheme:

The compounds of the invention can be synthesized using the methods described in the following schemes, examples, and by using art recognized techniques. All compounds described herein are included in the invention as compounds. Compounds of the invention may be synthesized according to at least one of the methods described in schemes 1 and 2.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, ag with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds according to of formula I can be prepared according to the Schemes provided infra.

The compounds of the invention of formula III can be prepared by hydrolysis of intermediate A wherein $P^1$ is an appropriate protecting groups selected from, but not limited to, methyl, ethyl, isopropyl, tert-butyl, methoxybenzyl or benzyl.

Intermediate A

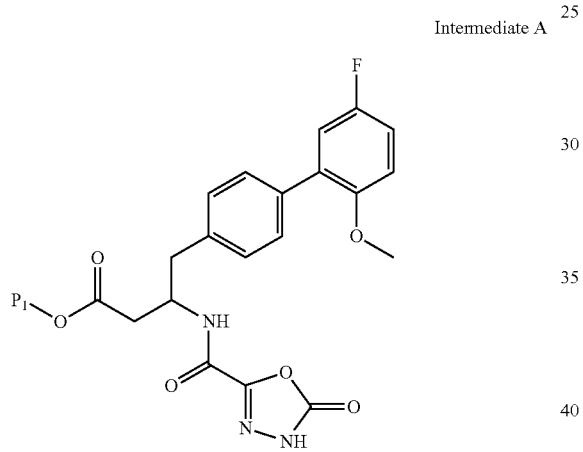

Standard methods can be applied for the hydrolysis of Intermediate A using a base selected from, but not limited to, NaOH, KOH or LiOH, or an acid selected from, but not limited to, TFA or HCl. When $P^1$ is benzyl or methoxybenzyl, preferable method of deprotection is hydrogenation in the presence of a catalyst such as, but not limited to, palladium-on-carbon under hydrogen.

The intermediate A can be prepared according to Scheme 1:

Scheme 1

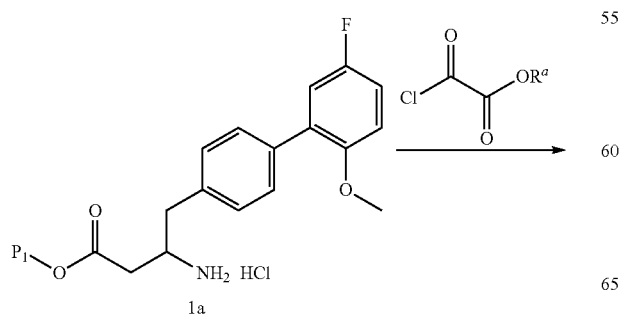

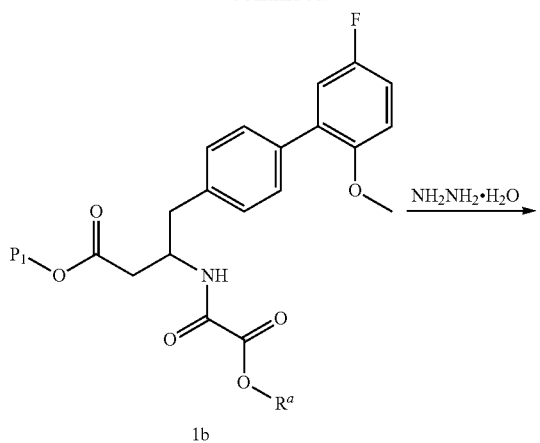

1b

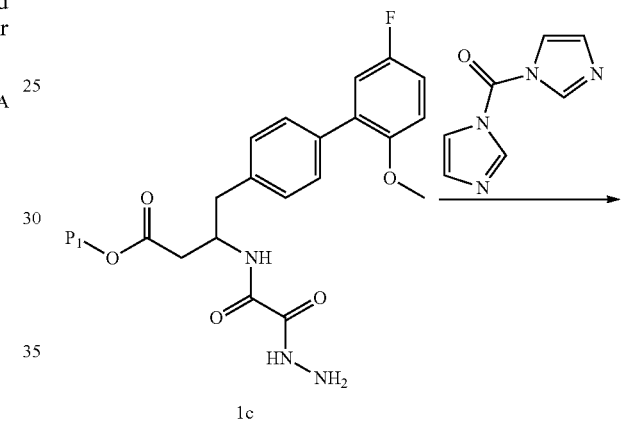

1c

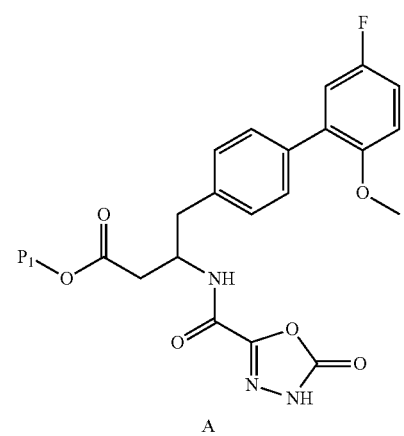

A

Intermediate 1a can be converted to intermediate 1b using ClC(O)C(O)OR$^a$ (wherein R$^a$ is $C_{1-7}$alkyl, halo-$C_{1-7}$alkyl or $C_{6-10}$aryl) and a base including but not limited to pyridine, triethylamine or diisopropylethylamine. Intermediate 1b can be converted to intermediate 1c using hydrazine hydrate. Intermediate 1c can be converted to intermediate A using carbonyldiimidazole or the like.

Intermediate 1a can be synthesized as described in Scheme 2:

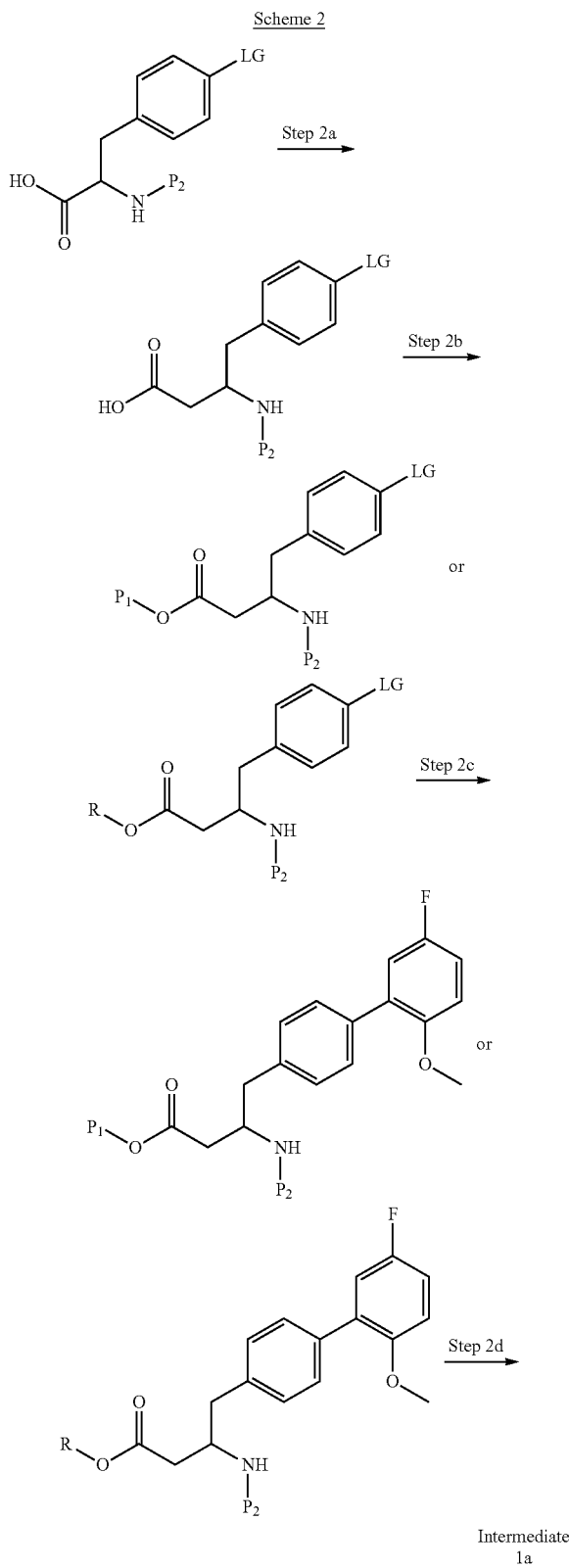

Scheme 2

Intermediate 1a wherein LG is a leaving group selected from, but not limited to, Cl, Br, I, OMs, OTs or OTf, $P^1$ is as previously defined and $P^2$ is an amino protecting group for example selected from t-Butyl, benzyl, triphenylphosphynyl, t-Butoxycarbonyl, benzyloxycarbonyl, allyloxycarbonyl, acetyl and trifluoroacetyl and R is $C_{1-7}$alkyl or $C_{6-10}$aryl.

In step (2a), standard methods for Arndt-Eistert homologation can be employed. An illustrative example of this chemistry is outlined in "Enantioselective synthesis of β-amino acids, $2^{nd}$ Edition", John Wiley and Sons, Inc., NJ (2005), either directly or analogously. Alternatively, 4-(4-bromophenyl)-3-((tert-butoxycarbonyl)amino)butanoic acid is commercially available in enantiomeric pure forms ((R) is CAS#331763-75-8 and (S) is CAS#270062-85-6) and can therefore be purchased from various commercial sources. For examples, (R)-enantiomer can be purchased from HBCChem Inc, with a catalog number of HBC2251.

In step (2b), standard methods to protect/alkylate the carboxylic acid can be employed, such as using $TMSCHN_2$ (for methyl ester), $P^1LG$ or RLG/base (e.g. $K_2CO_3$, $NaHCO_3$, $Cs_2CO_3$ or $K_3PO_4$), thionyl chloride (or oxalyl chloride)/ROH or $P^{10}H$, DCC (or EDCI)/DMAP/ROH or $P^{10}H$, BOP/ROK (or RONa), $(RO)_2CHNMe_2$, CDI/DBU/ROH (or $P^1OH$) wherein $P^1$ is selected from methyl, ethyl, t-Butyl, Allyl, benzyl, 4-methoxybenzyl.

In step (2c), standard methods for Suzuki coupling reaction can be applied, such as using a palladium (or nickel) species [e.g. $Pd(PPh_3)_4$, $PdCl_2(dppf)$, $Pd(OAc)_2$/a phosphine (e.g. $PPh_3$, dppf, $PCy_3$, $P(tBu)_3$, XPhos), Pd/C, $Pd_2(dba)_3$/a phosphine (e.g. $PPh_3$, dppf, $PCy_3$, $P(tBu)_3$, XPhos), $Ni(COD)_2$/a phosphine (or dppe, dppb, $PCy_3$), $Ni(dppf)Cl_2$], a base (e.g. KF, CsF, $K_3PO_4$, $Na_2CO_3$, $K_2CO_3$, $Cs_2CO_3$, NaOH, KOH, NaO-t-Bu, KO-t-Bu), and $(R^2)n$-$PhB(OH)_2$ [or $(R^2)n$-$PhBF_3K$].

In step (2d), standard methods for removing $P_2$ protecting groups can be applied, such as base hydrolysis using NaOH, KOH, or LiOH, acid hydrolysis using TFA or HCl, or hydrogenation using palladium-on-carbon under hydrogen.

Alternatively, step (2c) according to Scheme 2 may be carried out before step (2b).

Alternatively, the intermediate 1a may be prepared be following the synthetic routes outlined in *Tetrahedron Letters*, 2008, Vol. 49, No. 33, pp. 4977-4980 either directly or analogously and converting the obtained boronic acid into a substituted biphenyl by methods outlined in *Organic Letters*, 2002, Vol. 4, No. 22, pp. 3803-3805.

Alternatively, the intermediate 1a may be prepared be following the synthetic routes outlined in *Tetrahedron: Asymmetry*, 2006, Vol. 17, No. 2, pp. 205-209 either directly or analogously.

Alternatively, the intermediate 1a may be prepared by methods of Mannich reaction. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate 1a may be prepared by enolate addition. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate 1a may be prepared by methods of aza-Michael reaction. Illustrative examples of this chemistry are outlined in "Enantioselective synthesis of β-amino acids, $2^{nd}$ Edition", John Wiley and Sons, Inc., NJ (2005), either directly or analogously.

Alternatively, the intermediate 1a may be prepared following the synthetic route outlined in *Synlett*, 2006, No. 4, pp. 539-542, either directly or analogously.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention or a pharmaceutically acceptable salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers" include, but are not limited to, antioxidants such as ascorbic acid, pH buffers, or salt buffers, etc.

The compounds according to any one of formulae I to III, or a pharmaceutically acceptable salt thereof, in free form or in pharmaceutically acceptable salt form, exhibit valuable pharmacological properties, e.g. neutral endopeptidase modulating properties, e.g. as indicated in in vitro and in vivo tests as provided in the next sections and are therefore indicated for therapy.

Compounds of the invention or a pharmaceutically acceptable salt thereof, may be useful in the treatment of an indication selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunctions, hyperreninaemia, cystic fibrosis, restenosis, type-2 diabetes, metabolic syndrome, diabetic complications, atherosclerosis, and male and female sexual dysfunction. Thus, as a further embodiment, the present invention provides the use of a compound according to any one of formulae I to III, or a pharmaceutically acceptable salt thereof. In a further embodiment, the therapy is selected from a disease which is associated with neutral endopeptidase activity. In another embodiment, the disease is selected from the afore-mentioned list, suitably hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure (including edema and salt retention), diabetic nephropathy, non-diabetic nephropathy, contrast induced nephropathy, type-2 diabetes, and diabetic complications and most suitably cardiovascular disorders, such as hypertension, renal insufficiency including edema and congestive heart failure.

Thus, as a further embodiment, the present invention provides the use of a compound according to any one of formulae I to III, or a pharmaceutically acceptable salt thereof, in therapy. In a further embodiment, the therapy is selected from a disease which may be treated by inhibiting neutral endopeptidase activity.

In another embodiment, the invention provides a method of treating a disease which is associated with neutral endopeptidase activity comprising administration of a therapeutically acceptable amount of a compound according to any one of formulae I to III, or a pharmaceutically acceptable salt thereof. In a further embodiment, the disease is selected from the afore-mentioned list, suitably hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure (including edema and salt retention), diabetic nephropathy, non-diabetic nephropathy, contrast induced nephropathy, type-2 diabetes, and diabetic complications and most suitably cardiovascular disorders, such as hypertension, renal insufficiency including edema and congestive heart failure.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro and in vivo methods and/or by the following in vitro and in vivo methods well-described in the art. See Doering K, Meder G, Hinnenberger M, Woelcke J, Mayr L M, Hassiepen U, (2009) "A fluorescence lifetime-based assay for protease inhibitor profiling on human kallikrein 7", Biomol Screen, January; 14(1): 1-9.

In particular, the in vitro inhibition of recombinant human neutral endopeptidase can be determined as follows:

Recombinant human neutral endopeptidase (expressed in insect cells and purified using standard methods, final concentration 7 pM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys (PT14)-Arg-Arg-Leu-Trp-OH to a final concentration of 0.7 µM. Substrate hydrolysis leads to an increase in fluorescence lifetime (FLT) of PT14 measured by means of a FLT reader as described by Doering et al. (2009) as referenced supra. The effect of the compound on the enzymatic activity was determined after 1 hour (t=60 min) incubation at room temperature. The $IC_{50}$ values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory potency in accordance to Table 1, provided infra.

TABLE 1

Inhibitory Activity of Compounds

| Compounds: Example # | Human NEP $IC_{50}$ (nM) |
|---|---|
| Example 1 | 0.06 |

In particular, the in vivo inhibition of recombinant human neutral endopeptidase can be determined as follows:

ANP Potentiation Model

Natriuretic peptides are eliminated from the body via two primary pathways: 1) binding to natriuretic peptide clearance receptors followed by endocytosis and lysosomal hydrolysis and 2) hydrolysis by the membrane-bound zinc metalloprotease NEP, which has been identified in various tissues such as kidney, lung, intestine, brain, and neutrophils (Maack T (2006) The broad homeostatic role of natriuretic peptides. Arq Bras Endocrinol Metab; 50:198-207; Okolicany J, McEnroe G A, Koh G Y, et al (1992) Clearance receptor and neutral endopeptidase-mediated metabolism of atrial natriuretic factor. Am J Physiol; 263:F546-53.). In normal animals, the clearance receptor predominates in degrading natriuretic peptides (Maack 2006, referenced supra). In contrast, under conditions in which clearance receptors are saturated by high circulating levels of natriuretic peptides (e.g., congestive heart failure), the role of NEP in inactivating natriuretic peptides becomes significant (Maack 2006 referenced supra, Okolicany, et al 1992 referenced supra).

The latter observation was exploited to evaluate the peripheral effects of NEP inhibitors. By infusing exogenous ANP to saturate the clearance receptor, the ANP-metabolizing effects of NEP were unmasked in normal conscious rats (Gu, Jessie et al. (2010), "Pharmacokinetics and pharmacodynamics of LCZ696, a novel dual-acting angiotensin receptor-neprilysin inhibitor (ARNi)", Journal of Clinical Pharmacology, 50(4), 401-414, Okolicany, et al 1992 referenced supra, Trapani A J, Beil M E, Bruseo C W, et al (2004) CGS 35601 and its orally active prodrug CGS 37808 as triple inhibitors of endothelin-converting enzyme-1, neutral endopeptidase 24.11, and angiotensin-converting enzyme. J Cardiovasc Pharmacol; 44(Suppl 1):S211-5.). Thus, the potentiation of plasma ANP was used as an index of the extent and duration of inhibition of peripheral NEP by the orally administered compounds.

Adult, male Wistar Han (WH) rats (body weights: 470±50 g, mean±SD; age: 8.7-10.5 months) were purchased from Charles River Labs. They were housed on a 12-hr light/dark cycle (light: 6 am to 6 pm) at temperature and relative humidity set points of 72° F. and 55%, respectively. Rats were provided normal chow (Harlan Teklad 8604) and water ad libitum except for a partial fast before and during an experiment. In this case, the evening before the experiment (~5 pm) all but two of the rat's chow pellets were removed. On the morning of the experiment, any remaining food was removed. In most cases, however, both of the pellets were consumed overnight. Food was returned at the experiment terminus.

Rats were surgically instrumented with catheters to allow collection of arterial blood samples and intravenous (i.v.) administration of ANP. Rats were anesthetized and maintained in a surgical plane of anesthesia with isoflurane (2% in 100% oxygen). Ophthalmic lubricant was applied to each eye to prevent corneal irritation. Meloxicam (0.2 mg/kg s.c.) was administered for analgesia. If necessary for pain management, a second injection of meloxicam was administered on the first post-operative day. Also, a dose of penicillin G (50,000 U/kg i.m.) was administered pre-operatively to prevent infection.

Under aseptic surgical conditions, a femoral artery and vein were isolated and catheters inserted. Catheters consisted of a ~55-cm length of Tygon (PVC) Microbore tubing (0.020", 0.060" O.D.) bonded with cyclohexanone to a 4.5-cm length of polyurethane (0.012" I.D., 0.025" O.D., Micro-Renathane type MRE-025, Braintree Scientific, Inc., Braintree, Mass.) tubing. The catheters were tunneled subcutaneously and exteriorized in the mid-dorsal thoracic/abdominal region. Catheters exited through a subcutaneously anchored tether/swivel system which allowed the animal to move unrestrained in a specialized Plexiglas cage with perforated solid flooring. Catheters were flushed with sterile 0.9% saline and locked with 200 U/mL heparin in sterile 0.9% saline after the surgery was completed.

The rats were allowed to recover for at least one week before being studied while conscious and unrestrained. Rats were infused intravenously (450 ng/kg/min) with rat ANP (ANP (1-28), Product #14-5-41, American Peptide Company, Inc., Sunnyvale, Calif.). After 1 hr of ANP infusion, rats were treated by oral gavage with 1 mL/kg of vehicle (0.5% methylcellulose+0.1% Tween 80) or a selected dose of NEP inhibitor. ANP infusion was continued for an additional 8 hr. Arterial blood samples (0.20 mL) were withdrawn from the femoral arterial cannulas at various times (baseline or time 0, 0.25, 0.5, 1, 2, 4, 6, and 8 hr) into a collection tube containing 0.004 mL EDTA/protease inhibitor (PI) cocktail. Blood samples were centrifuged at 4° C. and 20K g to separate plasma. Plasma samples were aliquoted and frozen (−70° C.) for later analysis of plasma ANP (PANP) levels. The 0— to 8-hr time-weighted averages of the PANP concentrations expressed as a percent of the baseline (time 0) PANP values were used to generate dose-response relationships.

The blood collection cocktail consisted of broad-spectrum serine and cysteine PIs and EDTA. This combination was determined (in in vitro ANP-spiking experiments in whole blood) to prevent loss of ANP in the resulting plasma when incubated at 37° C. It also anticoagulated the blood.

The following ingredients were used for preparing the EDTA/PI cocktail:

1. EDTA-free Complete PI Cocktail Tablets (Roche Catalog #11 873 580 001)
2. K3EDTA from Vacutainer Blood Collection Tubes (Product #366450; Lavender conventional closure; ~Volume Draw: 7 mL; Liquid Additive: K3EDTA 15% solution, 0.081 mL, 12.15 mg)

The cocktail was prepared as follows:

1. Dissolve 2 full-size PI tablets in 0.94 mL of Millipore water (final volume is 1.0 mL=100× concentrated solution). Tablets will dissolve in ~1 min with vortexing.
2. Add 1.0 mL EDTA to the above PI solution. Vortex to mix well. Solution should be clear.
3. Divide the mixture into aliquots and freeze at −70° C. (stable for at least 12 weeks when frozen).

On the day of an experiment, a tube of EDTA/PI cocktail was thawed and stored on ice for use during the experiment. Likewise, the blood collection tubes containing this cocktail were stored on ice until the time of blood collection to minimize the breakdown of the PI.

PANP concentrations were measured with a commercial enzyme immunoassay kit (Atrial Natriuretic Factor (1-28)

(human) EIA kit, S-1131; Peninsula Laboratories, Inc., San Carlos, Calif.). The frozen plasma sample was thawed on ice and 10 µL of plasma was diluted 1:10 in 1× assay buffer supplied with the kit. Ten µL of the diluted sample was then assayed. The manufacturer's instructions were followed for the assay protocol (total volume per well was expanded to 50 µl with 1× assay buffer). Absorbance was read (Molecular Devices SpectraMax Paradigm Multi-Mode Detection Platform) at 450 nm within ten minutes of the assay termination. The linear range of the standard curves used for the extrapolation of the ANP concentration of the samples was between ~8 and 500 pg/well. The $IC_{50}$ values for the standard curves were 24.5±3.6 pg/well (mean±SD).

Using the in vivo assay (as described supra) compound of the invention exhibited superior in vivo efficacy compared to compound of Example 5.46 of WO 2010/136493, in accordance to Table 2, provided infra.

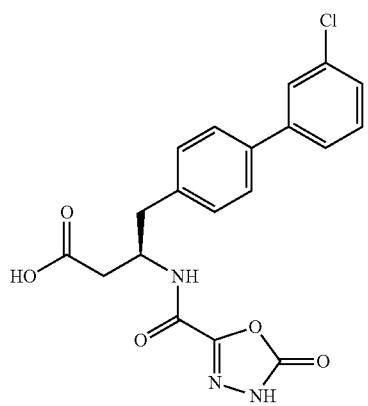

Example 5-46 of
WO2010/136493

In vivo superior efficacy of Example 1 compared to Example 5-46 of WO2010/136493 (PCT/EP2010/057247)

TABLE 2

| | Example 1 | | Example 5-46 of WO2010/136493 | |
|---|---|---|---|---|
| dose (mg/kg) | PANP % of baseline | SEM | PANP % of baseline | SEM |
| 1 | 141 | 16 | | |
| 3 | 183 | 11 | 137 | 14 |
| 10 | 238 | 6 | 126 | 19 |
| 30 | | | 185 | 10 |
| 100 | | | 254 | 67 |

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound according to any one of formulae I to III, or a pharmaceutically acceptable salt thereof, and at least one other therapeutic agent as a combined preparation for simultaneous, separate or sequential use in therapy. In one embodiment, the therapy is the treatment of a disease or condition associated with neutral endopeptidase activity.

Products provided as a combined preparation include a composition comprising the compound according to any one of formulae I to III, or a pharmaceutically acceptable salt thereof, and the other therapeutic agent(s) together in the same pharmaceutical composition, or the compound according to any one of formulae I to III, or a pharmaceutically acceptable salt thereof, and the other therapeutic agent(s) in separate form, e.g., in the form of a kit.

In one embodiment, the invention provides a pharmaceutical composition comprising a compound according to any one of formulae I to III, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to any one of formulae I to III, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g., in the case of a kit comprising the compound of the invention and the other therapeutic agent); (ii) by the physician themselves (or under the guidance of the physician) shortly before administration; (ii) in the patient themselves, e.g., during sequential administration of the compound of the invention and the other therapeutic agent. Accordingly, the invention provides the use of a compound according to any one of formulae I to III, or a pharmaceutically acceptable salt thereof, for treating a disease or condition associated with neutral endopeptidase activity, wherein the medicament is prepared for administration with another therapeutic agent. The invention also provides the use of another therapeutic agent for treating a disease or condition associated with neutral endopeptidase activity, wherein the medicament is administered with a compound according to any one of formulae I to III, or a pharmaceutically acceptable salt thereof.

The invention also provides a compound according to any one of formulae I to III, or a pharmaceutically acceptable salt thereof, for use in a method of treating a disease or condition associated with neutral endopeptidase activity, wherein the compound according to any one of formulae I to III, or a pharmaceutically acceptable salt thereof, is prepared for administration with another therapeutic agent. The invention also provides another therapeutic agent for use in a method of treating a disease or condition associated with neutral endopeptidase activity, wherein the other therapeutic agent is prepared for administration with a compound according to any one of formulae I to III, or a pharmaceutically acceptable salt thereof. The invention also provides a compound according to any one of formulae I to III, or a pharmaceutically acceptable salt thereof, for use in a method of treating a disease or condition associated with neutral endopeptidase activity, wherein the compound according to any one of formulae I to III or a pharmaceutically acceptable salt thereof, is administered with another therapeutic agent. The invention also provides another therapeutic agent for use in a method of treating a disease or condition associated with neutral endopeptidase activity, wherein the other therapeutic agent is administered with a compound according to any one of formulae I to III, or a pharmaceutically acceptable salt thereof.

The invention also provides the use of a compound according to any one of formulae I to III or a pharmaceutically acceptable salt thereof, for treating a disease or condition associated with neutral endopeptidase activity, wherein the patient has previously (e.g., within 24 hours) been treated with another therapeutic agent. The invention also provides the use of another therapeutic agent for treating a disease or condition associated with neutral endopeptidase activity, wherein the patient has previously (e.g., within 24 hours) been treated with a compound according to any one of formulae I to III, or a pharmaceutically acceptable salt thereof.

In one embodiment, the other therapeutic agent is selected from: HMG-Co-A reductase inhibitor, an anigiotensin receptor blocker (ARBs, angiotensin II receptor antagonist), angiotensin converting enzyme (ACE) inhibitor, a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor (ASI), a CETP inhibitor and a phophodiesterase type 5 (PDE5) inhibitor.

The term "in combination with" a second agent or treatment includes co-administration of the compound of the invention (e.g., a compound according to any one of Formulae I-III or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g a disorder or disease responsive to the inhibition of neutral endopeptidase, such as for example, hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications, atherosclerosis and male and female sexual dysfunction.

Examples of second agents include HMG-Co-A reductase inhibitors, angiotensin II receptor antagonists, angiotensin converting enzyme (ACE) inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), CETP inhibitors and phophodiesterase type 5 (PDE5) inhibitor.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbon*L-proly l-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]-alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

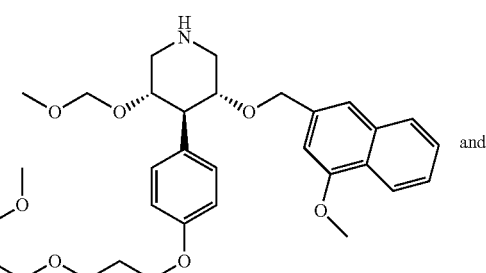

(A)

and (B)

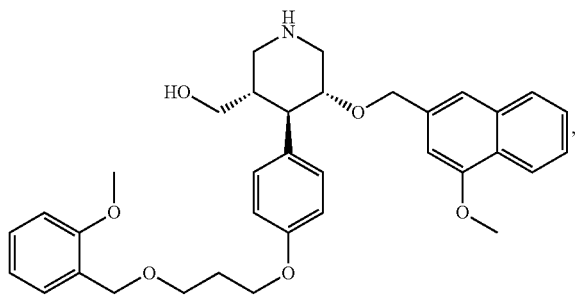

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which binds to the $AT_1$-receptor subtype of angiotensin II receptor but does not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

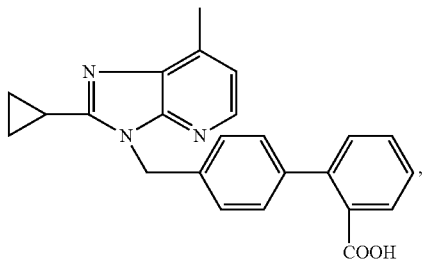 [SMILES: Cc1ccnc2c1nc(C1CC1)n2Cc1ccc(-c2ccccc2C(=O)O)cc1]

the compound with the designation SC-52458 of the following formula

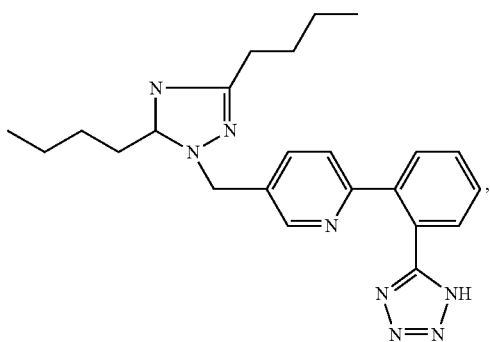 [SMILES: CCCCC1=NN(Cc2ccc(-c3ccccc3-c3nnn[nH]3)nc2)C(CCCC)N1]

and the compound with the designation ZD-8731 of the following formula

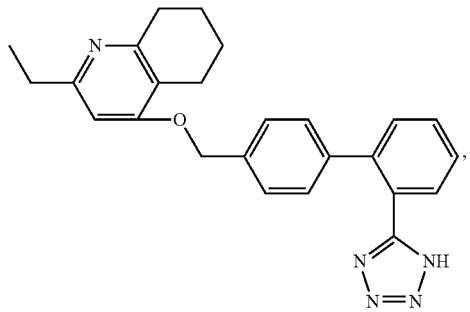 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonists are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F).

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

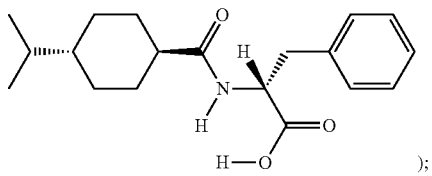 [SMILES: CC(C)[C@H]1CC[C@H](C(=O)N[C@H](Cc2ccccc2)C(=O)O)CC1]

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g., in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively. Other examples of DPP-IV inhibitor currently on the market are saxagliptin, sitagliptin, vidagliptin, and linagluptin.

GLP-1 is an insulinotropic protein which is described, e.g., by W. E. Schmidt et al. in *Diabetologia,* 28, 1985, 704-707 and in U.S. Pat. No. 5,705,483.

The term "GLP-1 agonists" includes variants and analogs of GLP-1(7-36)NH$_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy) phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]nnethyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α$_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the latter being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

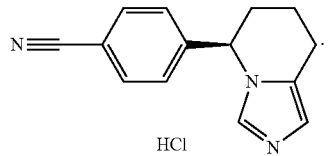 [SMILES: N#Cc1ccc([C@H]2CCCc3cncn32)cc1 ; Cl]

or, if appropriable, a pharmaceutically acceptable salt thereof.

A preferred steroidal aldosterone antagonist is eplerenone (cf. EP 122232 A) of the formula

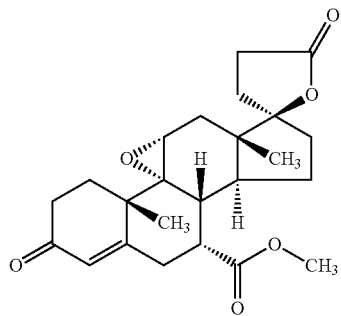

or spironolactone; or, in each case, if appropriable, a pharmaceutically acceptable salt thereof.

Aldosterone synthase inhibitors useful in said combination are compounds and analogs generically and specifically disclosed e.g., in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-d]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1, 4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5, 1-c][1,4]oxazine as developed by Speedel or in each case, the (R) or (S) enantiomer thereof; or if appropriable, a pharmaceutically acceptable salt thereof.

Aldosterone synthase inhibitors useful in said combination are compounds and analogs generically and specifically disclosed e.g., in WO 2009/156462 and WO 2010/130796, in particular in the compound claims and the final products of the working examples, the subject-matter of the final products, the pharmaceutical preparations and the claims.

Preferred aldosterone synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-yl}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl) ethanesulfonamide, N-((5-(3-chloro-4-cyanophenyl)-pyridin-3-yl)(cyclopropyl)methy)ethanesulfonamide, N-(cyclopropyl(5-(1H-indol-5-yl)pyridin-3-yl)methyl) ethanesulfonamide, N-(cyclopropyl(5-naphtalen-1-yl-pyridin-3-yl)methyl)ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyano-phenyl)-pyridin-3-yl]-cyclopropyl-methyl}-ethyl-amide.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl] amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot,* 49(8): 815-816 (1996), and *Bioorg. Med. Chem. Lett;* 6:1951-1954 (1996), respectively. Furthermore, the CETP inhibitors also include those disclosed in WO2000/017165, WO2005/095409 and WO2005/097806.

CETP inhibitors useful in said combination are compounds and analogs generically and specifically disclosed e.g., in WO 2008/009435, WO 2009/059943 and WO 2009/071509, in particular in the compound claims and the final products of the working examples, the subject-matter of the final products, the pharmaceutical preparations and the claims.

Examples of phophodiesterase type 5 (PDE5) inhibitors are sildenafil, avanafil, iodenafil, mirodenafil, tadalafil, vardenafil and udenafil.

Second agent of particular interest include endothelin antagonists, renin inhibitors, angiotensin II receptor antagonists, calcium channel blockers, diuretics, antidiabetic agents such as DPPIV inhibitors, aldosterone synthase inhibitors and/or phophodiesterase type 5 (PDE5) inhibitor.

In one embodiment, the invention provides a combination, in particular a pharmaceutical combination, comprising a therapeutically effective amount of the compound according to the definition of formula I, II or III a pharmaceutically acceptable salt thereof, and one or more therapeutically active agents selected from HMG-Co-A reductase inhibitors, angiotensin II receptor antagonists, angiotensin converting enzyme (ACE) inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI), CETP inhibitors and phophodiesterase type 5 (PDE5) inhibitor.

In one embodiment, the invention provides a method of inhibiting neutral endopeptidase activity in a subject, wherein the method comprises administering to the subject a therapeutically effective amount of the compound according to the definition of formula I, II or III or a pharmaceutically acceptable salt thereof.

In one embodiment, the invention provides a method of treating a disorder or a disease in a subject associated with neutral endopeptidase activity, wherein the method comprises administering to the subject a therapeutically effective amount of the compound according to the definition of formula I, II or III or a pharmaceutically acceptable salt thereof.

In one embodiment, the invention provides a method of treating a disorder or a disease in a subject associated with neutral endopeptidase activity, wherein the disorder or the disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Meniére's disease, hyperaldosteronism (primary and secondary), hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications, atherosclerosis, and male and female sexual dysfunction. In yet another embodiment, the invention provides a method of treating a disorder or a disease in a subject associated with neutral endopeptidase activity, wherein the disorder or the disease is selected from hypertension, pulmonary hypertension, isolated systolic hypertension, resistant hypertension, peripheral vascular disease, congestive heart failure and pulmonary arterial hypertension.

In one embodiment, the invention provides a compound according to the definition of formula I, II or III, or a pharmaceutically acceptable salt thereof, for use as a medicament.

In one embodiment, the invention provides the use of a compound according to the definition of formula I, II or III or a pharmaceutically acceptable salt thereof, for the treatment of a disorder or disease in a subject associated with neutral endopeptidase activity.

In one embodiment, the invention provides the use of a compound according to the definition of formula I, II or III, in the manufacture of a medicament for the treatment of a disorder or disease in a subject characterized by an activity of neutral endopeptidase, wherein said disorder or disease is in particular selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Meniére's disease, hyperaldosteronism (primary and secondary), hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications, atherosclerosis, and male and female sexual dysfunction. In yet another embodiment, the invention provides the use of a compound according to the definition of formula I, II or III, in the manufacture of a medicament for the treatment of a disorder or disease in a subject characterized by an activity of neutral endopeptidase, wherein said disorder or disease is in particular selected hypertension, pulmonary hypertension, isolated systolic hypertension, resistant hypertension, peripheral vascular disease, congestive heart failure and pulmonary arterial hypertension.

In one embodiment, the invention provides the use of a compound according to the definition of formula I, II or III, or a pharmaceutically acceptable salt thereof, for the treatment of a disorder or disease in a subject characterized by an activity of neutral endopeptidase, wherein the disorder or disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retention), cyclical oedema, Menière's disease, hyperaldosteronism (primary and secondary), hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications, atherosclerosis, male and female sexual dysfunction, and more particularly the disease or disorder is selected from hypertension, pulmonary hypertension, isolated systolic hypertension, resistant hypertension, peripheral vascular disease, congestive heart failure and pulmonary arterial hypertension.

EXEMPLIFICATION OF THE INVENTION

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Exemplification of the Invention

Abbreviations

| | |
|---|---|
| br: broad | bs: broad singlet |
| ACN: acetonitrile | d: doublet |
| dd: doublet of doublets | PANP: plasma atrial natriuretic peptides |
| EDTA: Ethylenediaminetetraacetic Acid | EIA: enzyme immunoassay |
| ES: electrospray | SEM: standard error of the mean |
| d: doublet | dd: doublet of doublets |
| HPLC: high pressure liquid chromatography | LC and LCMS: liquid chromatography and liquid chromatography and mass spectrometry |
| HPLC-RT (retention time) | |
| H: Hour(s) | hrs: hours |
| MS: mass spectrometry | m: multiplet |
| min: minutes | m/z: mass to charge ratio |
| UV: ultraviolet | MeOH: methanol |
| M and mM: Molar and millimole(s) | Mg: milligram |
| PVC: polyvinyl chloride | NMR: nuclear magnetic resonance |
| q: quartet | t: triplet |
| s: singlet | m: multiplet |
| TFA: trifluoroacetic acid | THF: tetrahydrofuran |
| μL, mL and L: microlitre, millilitre and litre | UV: ultraviolet |

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Analytical LCMS and HPLC-UV Methods:
LCMS Method 1:

| | |
|---|---|
| Mass Spectrometer: | Agilent 1100 series with Single Quad, Dual Mode mass spectrometer/API 2000, Triple Quad, ESI |
| Column: | Mercury MS Synergi 2 μ Max-RP 20 × 4.0 mm |

| Flow: | 2.0 mL/min |
| Mobile Phase: | A-0.1% Formic acid in water |
| | B-Acetonitrile |

| Gradient |
| Temp.: 30° C. |

| Time | % A | % B |
| --- | --- | --- |
| 0 | 70 | 30 |
| 0.5 | 70 | 30 |
| 1.5 | 5 | 95 |
| 2.4 | 5 | 95 |
| 2.5 | 70 | 30 |
| 3.0 | 70 | 30 |

HPLC-UV Method 2:

| Zorbax Eclipse XDB, C18, 4.6 × 150 mm, 5 μ, 1 mL/min |

| A-0.01% TFA in Water |
| B-Acetonitrile: Methanol (1:1) |

| Gradient |
| Temp.: 40° C. |
| Flow: 1.0-1.5 mL/min |

| Time | % A | % B |
| --- | --- | --- |
| 0 | 70 | 30 |
| 1 | 30 | 70 |
| 6 | 0 | 100 |
| 8 | 0 | 100 |
| 10 | 70 | 30 |
| 12 | 70 | 30 |

UPLCMS Method 3:
Aquity UPLC with Acquity Single Quad Mass Spectrometer, CSH C18 1.7 μM 2.1×50 mm, A: water 0.05% formic acid+ 3.75 mM NH₄Ac, B: acetonitrile 0.04% formic acid+3.75 mM NH₄Ac, 2%-98% over 2 min, 1 mL/min
HPLC-UV Method 4:
Atlantis C18 4.6×150 mm, A: water 0.1% TFA, B: ACN 0.05% TFA, 0%-95% over 20 min, 1 mL/min
The (R)-stereochemistry of Example 1 was attributed based on the known absolute stereochemistry of the synthetic intermediate [(R)-ethyl 3-amino-4-(5'-fluoro-2'-methoxy-[1,1-biphenyl]-4-yl)butanoate hydrochloride] as described in WO 2010/136493 (PCT/EP2010/057247) which is used as a starting material in the synthesis described infra. WO2010/136493 described the synthesis of (R)-ethyl 3-amino-4-(5'-fluoro-2'-methoxy-[1,1-biphenyl]-4-yl)butanoate hydrochloride starting from Boc-(R)-3-Amino-4(4-bromophenyl)butyric acid which was purchased from HBC-Chem, Inc. (Catalog #: HBC2251) as an enantiomerically pure compound. Under the reaction conditions, the chiral center is not expected to racemize.

EXAMPLE 1

Synthesis of (R)-4-(5'-fluoro-2'-methoxy-[1,1-biphenyl]-4-yl)-3-(5-oxo-4,5-dihydro-1,3,4-oxadiazole-2-carboxamido)butanoic acid

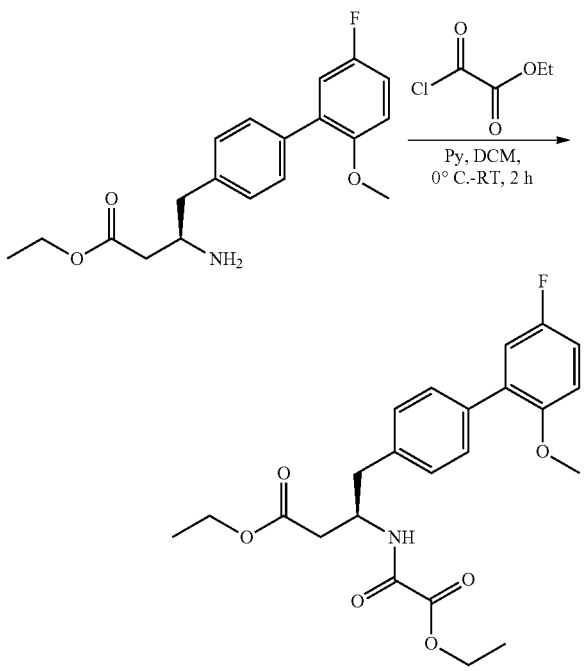

A: (R)-ethyl 3-(2-ethoxy-2-oxoacetamido)-4-(5'-fluoro-2'-methoxy-[1,1'-biphenyl]-4-yl)butanoate To a solution of (R)-ethyl 3-amino-4-(5'-fluoro-2'-methoxy-[1,1-biphenyl]-4-yl)butanoate hydrochloride (prepared as described in WO 2010/136493 (PCT/EP2010/057247) Intermediate 26) (6 g, 16 mmol) and pyridine (1.95 mL, 24 mmol) in dichloromethane at 0° C. was added a solution of ethyl 2-chloro-2-oxoacetate in dichloromethane (total reaction volume 120 mL). The reaction mixture was allowed to warm to room temperature and stirred for 2 hours. The reaction mixture was extracted by water and the aqueous layer was re-extracted with dichloromethane. The combined organic layers were extracted with saturated aqueous sodium chloride, dried over sodium sulfate and concentrated to afford a yellow oil that was purified by silica gel chromatography (40% ethyl acetate/hexanes) to afford 5.69 g (82%) of (R)-4-(5-fluoro-2'-methoxy-[1,1'-biphenyl]-4-yl)-3-(5-oxo-4,5-dihydro-1,3,4-oxadiazole-2-carboxamido)butanoic acid. LCMS Method 1 retention time 1.68 min ES+M+H(+) 432.2; LCUV Method 2 retention time 5.48 min; ¹H NMR (300 MHz, CHLOROFORM-d) δ ppm 7.73 (d, J=8.7 Hz, 1H), 7.46 (d, J=8.1 Hz, 2H), 7.24 (d, J=8.1 Hz, 2H), 6.89-7.06 (m, 3H), 4.50-4.51 (m, 1H), 4.34 (q, J=7.2 Hz, 2H), 4.17-4.20 (m, 2H), 3.78 (s, 3H), 2.91-3.10 (m, 2H), 2.58 (d, J=5.1 Hz, 2H), 1.38 (t, J=7.2 Hz, 3H), 1.29 (t, J=7.2 Hz, 3H)

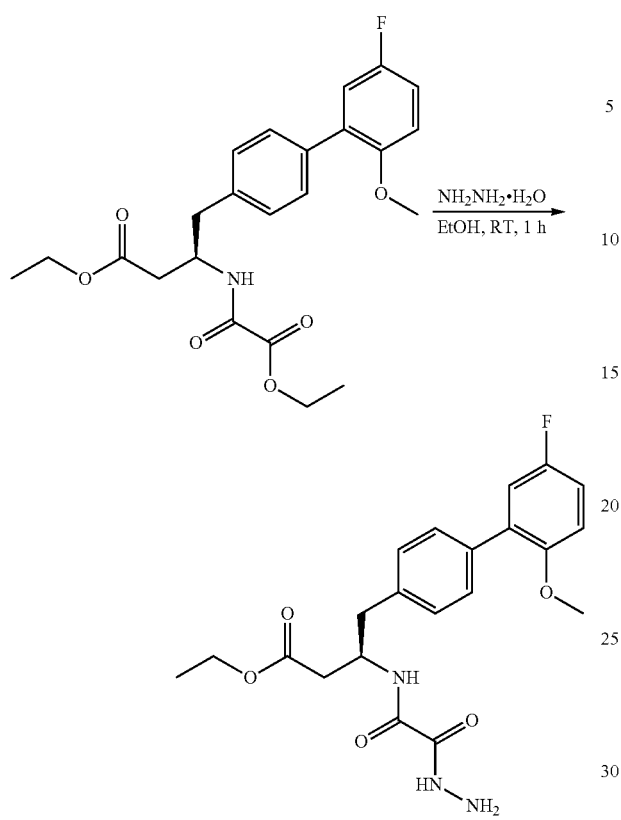

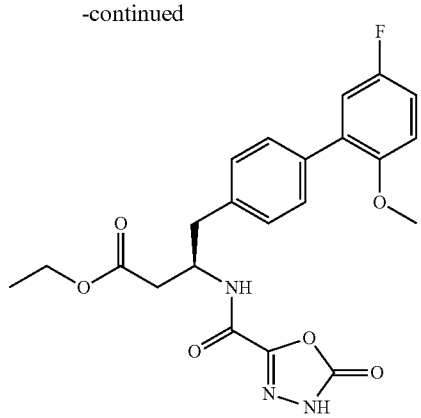

B: (R)-ethyl 4-(5'-fluoro-2'-methoxy-[1,1-biphenyl]-4-yl)-3-(2-hydrazinyl-2-oxoacetamido)butanoate To a solution of (R)-4-(5-fluoro-2'-methoxy-[1,1'-biphenyl]-4-yl)-3-(5-oxo-4,5-dihydro-1,3,4-oxadiazole-2-carboxamido)butanoic acid (5.9 g, 13.6 mmol) in ethanol (85 mL) was added hydrazine hydrate (0.8 mL, 16.4 mmol). The mixture was stirred 1 hour at room temperature. The resulting white precipitate was collected by filtration and washed with EtOH/Et$_2$O and dried to afford (R)-ethyl 4-(5'-fluoro-2'-methoxy-[1,1-biphenyl]-4-yl)-3-(2-hydrazinyl-2-oxoacetamido)butanoate 4.7 g (82%). LCMS Method 1 retention time 1.45 min ES+ M+H(+) 418.2; LCUV Method 2 retention time 4.66 min; $^1$H NMR (300 MHz, MeOH-d) δ ppm 7.42 (d, J=8.1 Hz, 2H), 7.25 (d, J=8.1 Hz, 2H), 7.00-7.03 (m, 3H), 4.50 (t, 1H), 4.10 (q, J=7.2 Hz, 2H), 3.76 (s, 3H), 2.92 (d, J=7.2 Hz, 2H), 2.62 (d, J=6.6 Hz, 2H), 1.23 (t, J=7.2 Hz, 3H)

C: (R)-ethyl 4-(5'-fluoro-2-methoxy-[1,1'-biphenyl]-4-yl)-3-(5-oxo-4,5-dihydro-1,3,4-oxadiazole-2-carboxamido)butanoate To a solution of (R)-ethyl 4-(5'-fluoro-2'-methoxy-[1,1'-biphenyl]-4-yl)-3-(2-hydrazinyl-2-oxoacetamido)butanoate (4.7 g, 11 mmol) in THF (115 mL) was added carbonyl diimidazole (2.4 g, 14 mmol) and the reaction mixture was stirred at room temperature for 24 hours then concentrated to a yellow oil than was purified by silica gel chromatography (40-45% ethyl acetate/hexane) to afford (R)-ethyl 4-(5'-fluoro-2'-methoxy-[1,1'-biphenyl]-4-yl)-3-(5-oxo-4,5-dihydro-1,3,4-oxadiazole-2-carboxamido)butanoate 4.25 g (84%). LCMS Method 1 retention time 1.57 min ES+ M+H(+) 443.8; LCUV Method 2 retention time 7.44 min; $^1$H NMR (400 MHz, MeOH-d) δ ppm 7.44 (d, J=8.0 Hz, 2H), 7.29 (d, J=8.0 Hz, 2H), 7.03-7.05 (m, 3H), 4.67 (t, 1H), 4.12 (q, J=7.2 Hz, 2H), 3.76 (s, 3H), 2.96 (d, J=6.8 Hz, 2H), 2.66 (d, J=6.8 Hz, 2H), 1.24 (t, J=7.2 Hz, 3H)

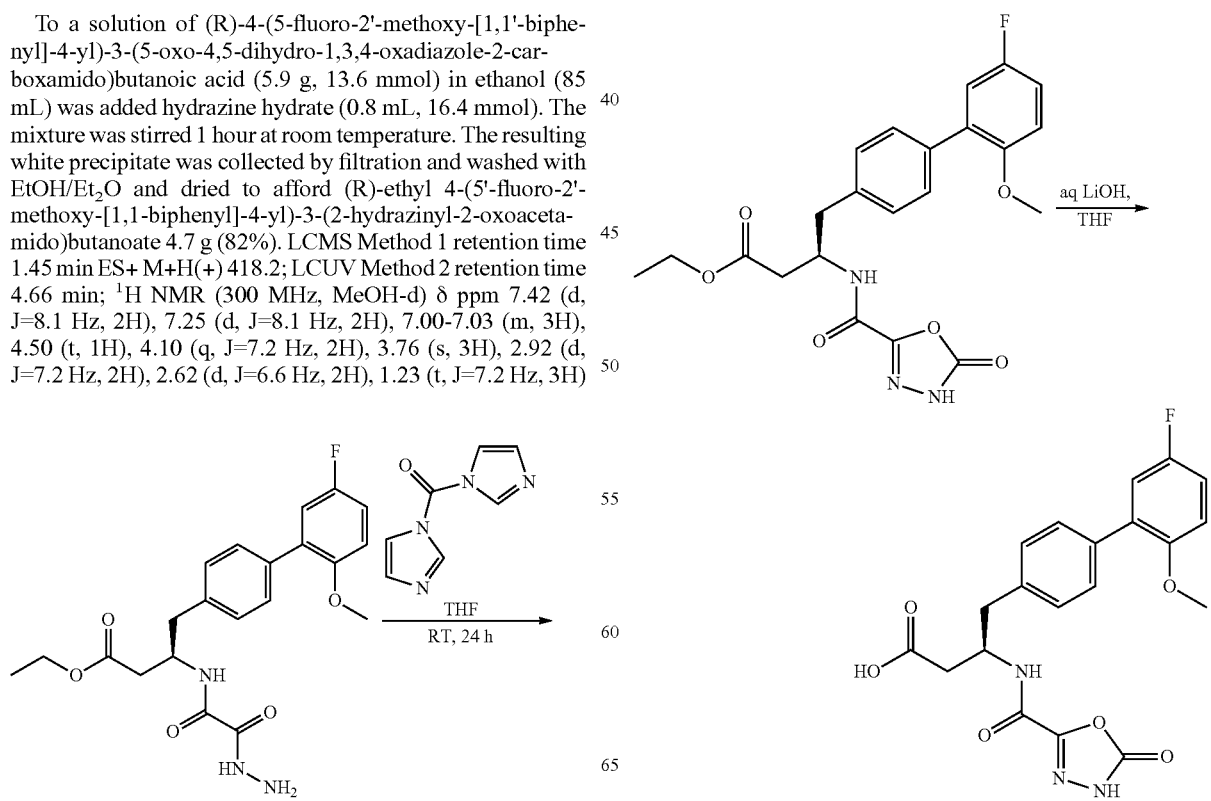

D: (R)-4-(5'-fluoro-2-methoxy-[1,1-biphenyl]-4-yl)-3-(5-oxo-4,5-dihydro-1,3,4-oxadiazole-2-carboxamido)butanoic acid To a solution of (R)-ethyl 4-(5'-fluoro-2'-methoxy-[1,1-biphenyl]-4-yl)-3-(5-oxo-4,5-dihydro-1,3,4-oxadiazole-2-carboxamnido)butanoate (4.25 g, 9.5 mmol) in THF (80 mL) and MeOH (20 mL) was added a solution of LiOH—H$_2$O (2.0 g, 47 mmol) in H$_2$O (20 mL). The reaction mixture was stirred for 3 hours at room temperature then concentrated. The residue was concentrated dissolved in water and washed with Et$_2$O. The aqueous layer was acidified with citric acid and extracted with ethyl acetate. The combined organic layer was dried over sodium sulfate and concentrated to obtain a solid (3.5 g, 88%). LCMS Method 1 retention time 1.24 min ES+ M+H(+) 416.4; LCUV Method 2 retention time 6.93 min; $^1$H NMR (400 MHz, MeOH-d) δ ppm 7.44 (d, J=8.0 Hz, 2H), 7.29 (d, J=8.0 Hz, 2H), 7.03-7.05 (m, 3H), 4.63-4.67 (m, 1H), 3.76 (s, 3H), 2.97 (d, J=7.2 Hz, 2H), 2.65 (d, J=7.2 Hz, 2H)

EXAMPLE 2

(R)-4-(5'-fluoro-2'-methoxy-[1,1-biphenyl]-4-yl)-3-(5-oxo-4,5-dihydro-1,3,4-oxadiazole-2-carboxamido)butanoic acid: Crystalline form A 113.1 mg of (R)-4-(5'-fluoro-2'-methoxy-[1,1-biphenyl]-4-yl)-3-(5-oxo-4,5-dihydro-1,3,4-oxadiazole-2-carboxamido)butanoic acid in an amorphous form (a batch prepared as in Example 1) was dissolved in 5.3 ml of ethanol:water (1:2 v/v) in 20 mL glass vial. The sample was set on stirring and the initially hazy solution became clear on stirring within ~15 min. The reaction mixture was stirred overnight @ 440 rpm. White precipitate was observed at this point. The reaction mixture was stirred for another 8 hours and then filtered. The filtered cake was washed with 2 mL ethanol:water (1:2 v/v). The washed cake was dried in oven at 40° C. at around 0.85 bar for 24 h. 73.2 mg (64.7% yield) of slightly off-white solid was obtained. The same crystalline Form A of (R)-4-(5'-fluoro-2'-methoxy-[1,1'-biphenyl]-4-yl)-3-(5-oxo-4,5-dihydro-1,3,4-oxadiazole-2-carboxamido)butanoic acid was obtained from at least six additional solvent system: after four heat-cool cycles (5° C.-55° C.) from ethyl acetate:heptane 1:9 (v/v), 1:4 (v/v), or 1:1 (v/v), and from Ethanol:heptane 1:4 (v/v), or 1:1 (v/v).

Form A
a) X-Ray Powder Diffraction

An x-ray powder diffraction pattern was recorded on a Bruker™ D8 GADDS Discover diffractometer with CuKα, anode (CuKα radiation (λ=1.5418 Å).

The X-ray diffraction pattern thus determined is shown in FIG. 1 and represented in Table 3 below by the reflection lines of the most important lines.

TABLE 3

| Angle 2-Theta ° | Intensity % |
|---|---|
| 6.837 | 35.7 |
| 8.473 | 59.1 |
| 10.94 | 15.5 |
| 13.711 | 37 |
| 14 | 20.8 |
| 15.841 | 38.2 |
| 16.987 | 71.2 |
| 17.633 | 68.3 |
| 18.716 | 23.3 |
| 20.036 | 43.6 |
| 20.976 | 14.9 |
| 21.554 | 15.9 |
| 21.858 | 16.6 |

TABLE 3-continued

| Angle 2-Theta ° | Intensity % |
|---|---|
| 23.436 | 22.7 |
| 24.772 | 21.4 |
| 25.291 | 97.2 |
| 25.791 | 95.9 |
| 26.628 | 100 |
| 27.781 | 36.7 |
| 28.056 | 42.4 |
| 29.332 | 18.1 |
| 32.708 | 16.8 |
| 33.944 | 23.1 |
| 34.524 | 26.2 |
| 35.773 | 22.6 | b) Elemental Analysis:
Water content (Karl Fischer titration): 0.16-0.3% m/m (mass/mass)

TABLE 4

| Element | theoretical content [% m/m] | measured content [% m/m] |
|---|---|---|
| C | 57.83 | 58.3 |
| H | 4.37 | 4.37 |
| N | 10.12 | 10.13 |
| F | 4.57 | 4.7 |
| O | 23.11 | 22.5 |

Experimental data correspond to expectations for a free acid of (R)-4-(5'-fluoro-2'-methoxy-[1,1'-biphenyl]-4-yl)-3-(5-oxo-4,5-dihydro-1,3,4-oxadiazole-2-carboxamido)butanoic acid c) Differential Scanning Calorimetry (DSC):
Differential scanning calorimetry (DSC) and thermogravimetric analysis trace of Form A was obtained using TA Instruments Q2000 (DSC) and Q5000 (TGA) with aluminium pan (TI20608); heating rate 10 C.°/min, temperature range: 25 to 300° C. Melting endotherm: $T_{onset}$=168.16° C., ΔH=90.77 J/g; small initial weigh loss of 0.77% before melt onset.
DSC:
Accurately weigh 0.5-1.0 mg of test substance into the closed sample pan. An empty sample pan is used as reference. Unless otherwise stated through the document, the DSC thermogram is recorded as follow: the temperature of the apparatus is adjusted to about −40° C., and heated to 300° C. at a heating rate of 10° C./min, under a nitrogen flow of 50 mL/min. The instrument is calibrated for temperature and enthalpy with Indium, at least 99.9999% pure. The accuracy of the measured sample temperature with this method is within about ±1° C., and the heat of fusion can be measured within a relative error of about ±5%.
TGA:
Accurately weigh 0.5-1.0 mg of test substance into the open sample pan. The TGA thermogram is recorded as follows: the sample is loaded into the furnace, the temperature equilibrated to 30° C. and heated to 300° C. at a heating rate of 10° C./min, under a flow of nitrogen at 25 m L/min.
The instrument is calibrated for temperature with nickel and aluminum, and calibrated for weight with a 100 mg standard.

It can be seen that the compounds of the invention are useful as inhibitors of Neutral endopeptidase activity and therefore useful in the treatment of diseases and conditions associated with Neutral endopeptidase activity such as the diseases disclosed herein. Additionally, the compounds of the invention have unexpected improved in vivo efficacy.

It will be understood that the invention has been described by way of example only and modifications may be made whilst remaining within the scope and spirit of the invention.

What is claimed is:

1. A compound of the formula (I):

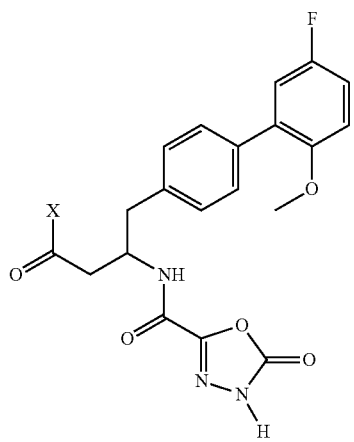

wherein:
X is OH, O—$C_{1-7}$alkyl or O—$C_{6-10}$aryl; or a pharmaceutically acceptable salt thereof.

2. The compound according to claim 1 of Formula II:

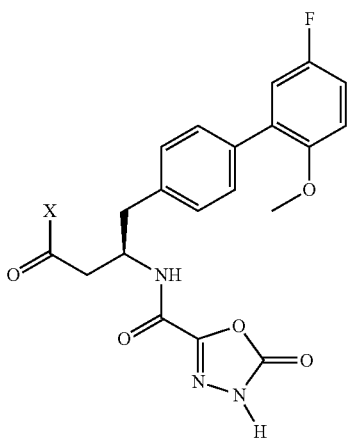

wherein:
X is OH, O—$C_{1-7}$alkyl or O—$C_{6-10}$aryl; or a pharmaceutically acceptable salt thereof.

3. The compound according to claim 2 having Formula III:

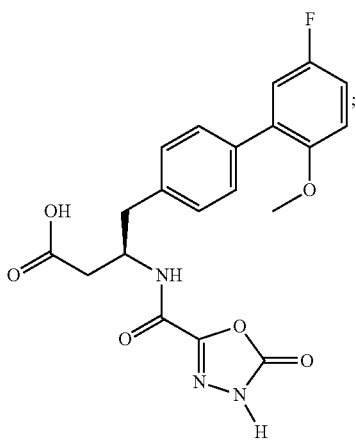

or a pharmaceutically acceptable salt thereof.

4. A pharmaceutical composition comprising a compound according to claim 1, or a pharmaceutically acceptable salt thereof and one or more pharmaceutically acceptable carriers.

5. A combination comprising: a compound according to claim 1 or a pharmaceutically acceptable salt thereof and one or more therapeutically active agents selected from HMG-Co-A reductase inhibitor, an anigiotensin receptor blocker, angiotensin converting enzyme Inhibitor, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor, a CETP inhibitor and a phophodiesterase type 5 (PDE5) inhibitor.

6. A method of inhibiting neutral endopeptidase activity in a subject in need thereof, comprising: administering to the subject a therapeutically effective amount of the compound according to claim 1 or a pharmaceutically acceptable salt thereof.

7. A method of treating a disorder or a disease associated with neutral endopeptidase activity in a subject in need thereof, comprising: administering to the subject a therapeutically effective amount of the compound according to claim 1 or a pharmaceutically acceptable salt thereof.

8. The method according to claim 7, wherein the disorder or the disease is selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labour, pre-eclampsia, endometriosis, and reproductive disorders, asthma, obstructive sleep apnea, inflammation, leukemia, pain, epilepsy, affective disorders, depression, psychotic condition, dementia, geriatric confusion, obesity, gastrointestinal disorders, wound healing, septic shock, gastric acid secretion dysfunction, hyperreninaemia, cystic fibrosis, restenosis, type-2 diabetes, metabolic syndrome, diabetic complications, atherosclerosis, and male and female sexual dysfunction.

9. The method according to claim 7, wherein the disorder or the disease is selected from hypertension, pulmonary hypertension, isolated systolic hypertension, resistant hypertension, peripheral vascular disease, congestive heart failure or pulmonary arterial hypertension.

10. A pharmaceutical composition comprising a compound according to claim 3, or a pharmaceutically acceptable salt thereof and one or more pharmaceutically acceptable carriers.

11. A combination comprising: a compound according to claim 3 or a pharmaceutically acceptable salt thereof and one or more therapeutically active agents selected from HMG-Co-A reductase inhibitor, an anigiotensin receptor blocker, angiotensin converting enzyme Inhibitor, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitor, a CETP inhibitor and a phophodiesterase type 5 (PDE5) inhibitor.

12. A method of inhibiting neutral endopeptidase activity in a subject in need thereof, comprising: administering to the subject a therapeutically effective amount of the compound according to claim 3 or a pharmaceutically acceptable salt thereof.

13. A method of treating a disorder or a disease associated with neutral endopeptidase activity in a subject in need thereof, comprising: administering to the subject a therapeutically effective amount of the compound according to claim 3 or a pharmaceutically acceptable salt thereof.

14. The method according to claim 13, wherein the disorder or the disease is selected from hypertension, resistant hypertension, pulmonary hypertension, pulmonary arterial hypertension, isolated systolic hypertension, peripheral vascular disease, heart failure, congestive heart failure, left ventricular hypertrophy, angina, renal insufficiency, renal failure, diabetic nephropathy, non-diabetic nephropathy, contrast-induced nephropathy, nephrotic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiomyopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure, cyclical oedema, Menière's disease, hyperaldosteronism, hypercalciuria, ascites, glaucoma, menstrual disorders, preterm labour, pre-eclampsia, endometriosis, and reproductive disorders, asthma, obstructive sleep apnea, inflammation, leukemia, pain, epilepsy, affective disorders, depression, psychotic condition, dementia, geriatric confusion, obesity, gastrointestinal disorders, wound healing, septic shock, gastric acid secretion dysfunction, hyperreninaemia, cystic fibrosis, restenosis, type-2 diabetes, metabolic syndrome, diabetic complications, atherosclerosis, and male and female sexual dysfunction.

15. The method according to claim 13, wherein the disorder or the disease is selected from hypertension, pulmonary hypertension, isolated systolic hypertension, resistant hypertension, peripheral vascular disease, congestive heart failure or pulmonary arterial hypertension.

* * * * *